US00PP30383P3

(12) United States Plant Patent
Farrow

(10) Patent No.: US PP30,383 P3
(45) Date of Patent: Apr. 16, 2019

(54) ***FLORIBUNDA* ROSE PLANT NAMED 'FARROWRSP'**

(50) Latin Name: *Rosa hybrida*
Varietal Denomination: FARROWRSP

(71) Applicant: Michael Wayne Farrow, Warwick, MD (US)

(72) Inventor: Michael Wayne Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/330,309

(22) Filed: Sep. 2, 2016

(65) Prior Publication Data

US 2018/0070488 P1 Mar. 8, 2018

(51) Int. Cl.
*A01H 5/02* (2018.01)
*A01H 6/74* (2018.01)

(52) U.S. Cl.
USPC ..... Plt./141
CPC ..... *A01H 5/02* (2013.01); *A01H 5/0222* (2013.01); *A01H 6/749* (2018.05)

(58) Field of Classification Search
USPC ..... Plt./101, 102, 141
See application file for complete search history.

*Primary Examiner* — Susan Beth McCormick Ewoldt
*Assistant Examiner* — Karen M Redden
(74) *Attorney, Agent, or Firm* — Cassandra Bright

(57) ABSTRACT

A new and distinct *Rosa* cultivar, for garden use named 'FARROWRSP' is disclosed, characterized by bright salmon and yellow colored flowers. Plants are distinctively compact and useful for small garden spaces and have an above average resistance to diseases. The new variety is a *Rosa*, normally produced as an outdoor garden or container plant.

2 Drawing Sheets

Latin name of the genus and species: *Rosa hybrida*.
Variety denomination: 'FARROWRSP'.

BACKGROUND OF THE INVENTION

The new *Rosa* cultivar is a product of a chance discovery by the inventor, Christopher Michael Farrow. The discovery was made during 2010 at a commercial nursery in Maryland. The new variety is the result of a naturally occurring branch mutation of *Rosa* 'ChewMayTime', U.S. Plant Pat. No. 18,347.

Asexual reproduction of the new cultivar was performed by softwood cuttings at a the same commercial nursery in Warwick, Md. during 2010. Subsequent propagation has shown that the unique features of this cultivar are stable and reproduced true to type in successive generations.

SUMMARY OF THE INVENTION

The cultivar 'FARROWRSP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FARROWRSP' These characteristics in combination distinguish 'FARROWRSP' as a new and distinct *Rosa* cultivar:

1. Bright salmon and yellow colored flowers.
2. Strong disease resistance.
3. Very compact plant habit.
4. Very good landscape performance in tight or small spaces.

Plants of the new cultivar 'FARROWRSP' are similar to plants of the parent in most horticultural characteristics, however, plants of the new cultivar 'FARROWRSP' differ in the following:

1. Flower color of the new variety is salmon, flower color of the parent is orange.

COMMERCIAL COMPARISON

Plants of the new cultivar 'FARROWRSP' can be compared to the commercial variety *Rosa* 'ChewperAdventure', unpatented. These varieties are similar in most horticultural characteristics; however 'FARROWRSP' differs in the following:

1. Flower color is salmon. Comparator flower is pink and orange.
2. The new variety has a single whorl of petals, compared to the semi-double whorl of this comparator.

Plants of the new cultivar 'FARROWRSP' can also be compared to the commercial variety *Rosa* 'Chewpatout', patented, U.S. Plant Pat. No. 28,395. These varieties are similar in most horticultural characteristics, including disease resistance and flower shape. However 'FARROWRSP' differs in the following:

1. Flower color is salmon. Comparator flower is red.

BRIEF DESCRIPTION OF THE PHOTOGRAPHS

Figure 1:
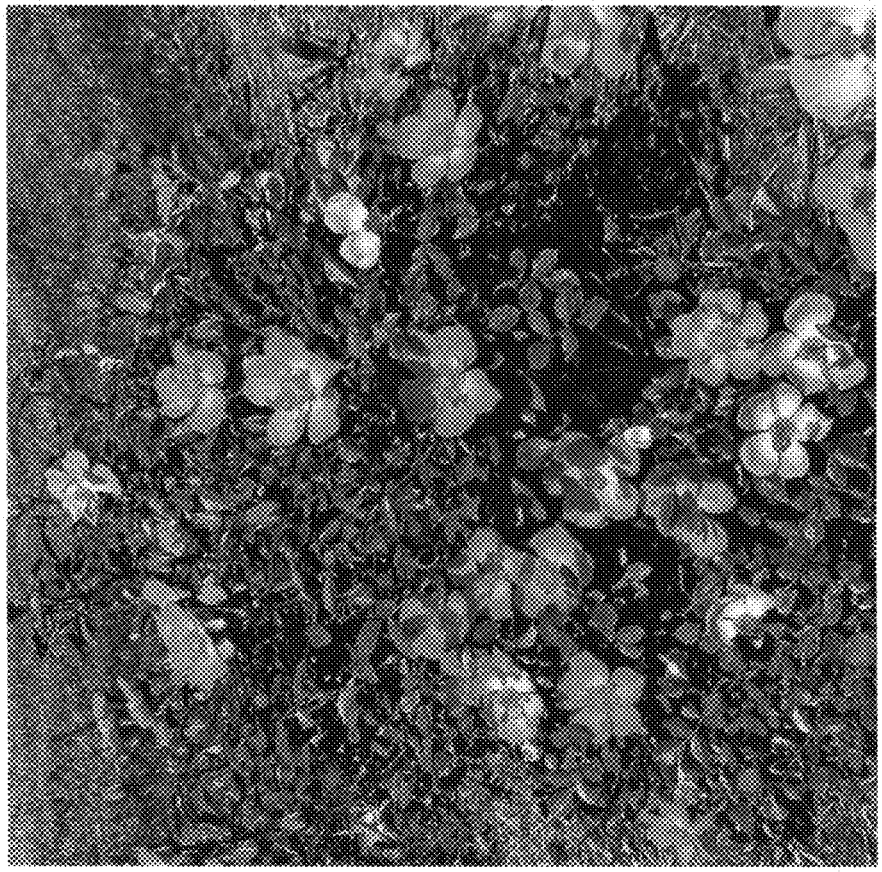

The accompanying photograph in FIG. 1 illustrates in full color a plant of 'FARROWRSP', growing in the ground in Michigan.

Figure 2:
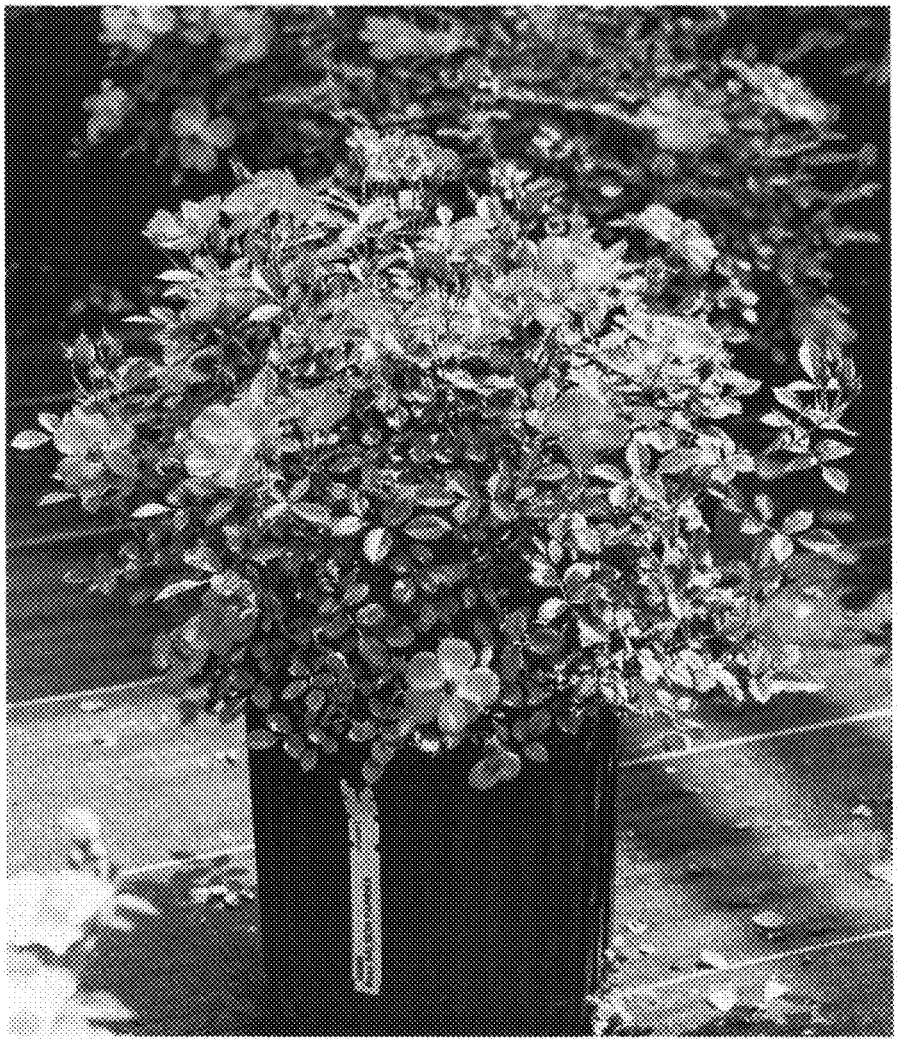

FIG. 2 illustrates a typical 2 year old plant of the new variety, in a 2 gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'FARROWRSP' plants grown in a poly house greenhouse, in Grand Haven, Mich. The growing temperature ranged from approximately 18° C. to 27° C. during the day and from approximately 5° C. to 10° C. during the night. General light conditions are bright, normal sunlight. Measurements and numerical values represent averages of typical plant types.

Botanical classification: *Rosa hybrida* 'FARROWRSP'.

Market classification: Floribunda garden rose.

Propagation:

*Time to initiate roots.*—About 30 days at approximately 20° C.

*Time to produce a rooted young plant.*—About 120 days at approximately 20° C.

*Root description.*—Moderately free branching, medium thickness, both fibrous and fleshy roots present. Roots a creamy white color, not accurately measured with R.H.S. chart.

Plant:

*Age of plant described.*—Approximately 2 to 3 years.

*Plant habit.*—Compact, upright and mounded garden rose.

*Container size of plant described.*—2 gallon.

*Height.*—20 cm.

*Plant spread.*—36 cm.

*Rootstock.*—Un-grafted, plants grown on own roots.

*Growth rate.*—Moderate.

*Branching arrangement.*—Low, dense, free branching. Pinching required.

*Lateral branches.*—Quantity: Average 4 major lateral branches, with many sub-laterals. Diameter: Approximately 3 mm. Length: Approximately 18 cm. Color: Near Yellow-Green 144A. Internode Length: Average 2.5 cm. Angle: Very upright growth, branches at narrow, acute angles. Strength: Strong. Texture: Glabrous, thorny. Thorns: Approximately density/quantity of thorns: 4 per linear cm. Shape: Subulate. Round base, acute apex. Color of thorns: Immature: Near Greyed-Orange 173B. Mature: Near Greyed-Orange 173D. Diameter: Average 1 mm at base. Height: Average 2 mm.

Foliage:

*Leaf.*—Arrangement: Opposite. Quantity: Approximately 34 per branch. Average Length: Approximately 8 cm. Average Width: Approximately 5 cm.

*Leaflet.*—Quantity: 3 to 5. Average Length: Terminal Length: Approximately 3.0 cm. Lateral Length: Approximately 2.0 cm. Average Width: Terminal Width: Approximately 1.5 cm. Lateral Width: Approximately 1.0 cm. Shape of blade: Ovate. Apex: Acuminate. Base: Acute. Margin: Serrulate. Appearance of top surface: Glossy. Appearance of bottom surface: Slightly glossy. Texture of top surface: Glabrous. Texture of bottom surface: Glabrous. Color: Young foliage upper side: Near Green 137B. Young foliage under side: Near Yellow-Green 146A. Mature foliage upper side: Near Green 137B. Mature foliage under side: Near Yellow-Green 146A. Venation: Type: Pinnate. Venation color upper side: Midrib near RHS Yellow-Green 145A. Lateral veins near 145B. Venation color under side: Midrib near RHS Yellow-Green 146D. Lateral veins near 146C. Petiole: Length: 2.5 cm. Width: 4 mm. Color: Upper surface near RHS Yellow-Green 145A; lower surface near 146D. Texture: Microthorns. Leaflet Petiole: Length: 1.0 mm. Width: 1.0 mm. Color: Upper surface near RHS Yellow-Green 145A; lower surface near 145B. Texture: Microthorns. Stipule: Quantity: 2. Shape: Linear/Acicular. Apex: Acicular. Base: Truncate, fused along petiole. Margin: Ciliate. Length: 1.25 cm. Width: 2 mm. Texture: Glabrous, upper and lower surfaces. Color: Upper surface near Yellow-Green 144A. Lower surface near Yellow-Green 144A. Foliage durability to stress: Good.

Flower:

*Natural flowering season.*—Spring through Summer.

*Arrangement.*—2 to 4 sprays of 2 to 4 flowers occurring at terminal branch ends. Evenly rotate, single whorl flowers.

*Flower size.*—Diameter: Approximately 5.0 cm. Depth: Approximately 5.0 cm.

*Petals.*—Petal arrangement: Rotate, slightly overlapping single whorl. Length: 2.25 cm. Width: 2.0 cm. Shape: Obovate. Margin: Entire. Apex: Retuse. Base: Obtuse. Petal quantity: Average 5 to 7. Texture: Glabrous, silky, upper and lower surfaces.

*Color.*—Petals: When opening: Upper surface: Near Orange-Red 34A. Lower surface: Near RHS Red 44B. Fully opened: Upper surface: Near Orange-Red 34A, basal blotch near Yellow 12A. Lower surface: Near Red 50A, basal blotch near Yellow 12A. Color Changes when aging: Upper surface: Near Red 50A, basal blotch enlarges, colored near Yellow 12C. Lower Surfaces: Near Red 50A, basal blotch enlarges, colored near Yellow 12C.

*Petaloids.*—Arrangement: Whorled. Quantity: 0 to 4. Length: 2.0 cm. Width: 1.0 cm. Shape: Irregular, close to obcordate. Margin: Entire. Texture: Glabrous, silky, upper and lower surfaces. Color: When opening, both surfaces: Near Red 43A, streaked Yellow 13A. Mature, both surfaces: Near Red 39A, streaked Yellow 12B.

*Bud.*—Shape: Ovate. Length: Approximately 2.0 cm. Diameter: Approximately 1.2 cm. Color: Near RHS Yellow-Green 144A.

*Sepals.*—Quantity: 5. Arrangement: Whorled. Length: 3.1 cm. Width: 0.9 cm. Shape: Aristate. Margin: Irregularly serrate. Apex: Acuminate. Base: Truncate. Color: Immature: Interior Surface: Near RHS Yellow-Green 146C. Exterior Surface: Near RHS Yellow-Green 148C. Mature: Interior Surface: Near RHS Yellow-Green 145A. Exterior Surface: Near RHS Yellow-Green 145B. Texture: Interior surface pubescent, exterior surface glabrous. Fragrance: Lightly sweet.

*Peduncle.*—Length: 2.5 cm. Diameter: 2 mm. Strength: Strong. Angle: Upright and outward approximately 75°. Texture: Thorny. Color: Near Yellow-Green 144A.

*Pedicel.*—Length: 3.25 cm. Diameter: 2 mm. Strength: Strong. Angle: Upright and outward. Texture: Glabrous with microthorns. Color: Near Yellow-Green 144A.

Reproductive organs:

*Stamens.*—Number: 100. Filament length: Approximately 1.5 cm. Filament color: Near RHS Orange 24B.

*Anthers*.—Length: 1.5 mm. Shape: Oblong. Color: Near RHS Yellow-Orange 22A. Pollen: Color: Near RHS Yellow-Orange 22A. Quantity: Moderate.

*Pistil*.—Quantity: 40. Length: 7 mm. Style: Length: Approximately 5.0 mm. Color: Near RHS Red 46B. Stigma: Shape: Globular cluster. Color: Near RHS Yellow-Orange 15B.

*Receptacle*.—Height: 7.5 mm. Diameter: 5.0 mm. Shape: Obovate. Texture: Smooth. Color: Near RHS Yellow-Green 144A.

Other characteristics:

*Seeds and fruits*.—Not observed to date.

*Disease/pest resistance*.—Above average disease resistance to normal diseases typical of garden roses. Average tolerance for typical garden pests.

What is claimed is:

1. A new and distinct cultivar of Floribunda rose plant named 'FARROWRSP', used as a garden rose, as herein illustrated and described.

* * * * *